US005803103A

United States Patent [19]

Haruyama

[11] Patent Number: 5,803,103

[45] Date of Patent: Sep. 8, 1998

[54] WALKER

[75] Inventor: Mitsuru Haruyama, Osaka, Japan

[73] Assignees: Handi Network International Co., Ltd., Osaka; Remotex Corporation, Tokyo, both of Japan

[21] Appl. No.: 880,642

[22] Filed: Jun. 23, 1997

[51] Int. Cl.[6] .......... A01H 3/00

[52] U.S. Cl. .......... 135/67; 135/72; 280/87.021

[58] Field of Search .......... 135/67, 72, 76; 482/66, 68; 297/5–7; 280/87.021, 87.01, 87.041; 188/156, 161, 163, 82.77, 82.3, 82.6

[56] References Cited

U.S. PATENT DOCUMENTS

| | | | |
|---|---|---|---|
| 2,686,571 | 8/1954 | Horste | 280/87.01 X |
| 4,703,769 | 11/1987 | Harrison, Jr. | 135/67 |
| 4,748,994 | 6/1988 | Schultz et al. | 135/67 |
| 4,770,410 | 9/1988 | Brown | 135/67 X |
| 5,026,080 | 6/1991 | Steffe et al. | 280/87.041 X |
| 5,255,697 | 10/1993 | Grauer | 135/67 |
| 5,390,753 | 2/1995 | Parker | 280/87.041 X |
| 5,538,268 | 7/1996 | Miller | 280/87.041 X |
| 5,603,517 | 2/1997 | Lorman | 135/67 X |

*Primary Examiner*—Lanna Mai
*Attorney, Agent, or Firm*—Wenderoth, Lind & Ponack, L.L.P.

[57] ABSTRACT

A walker adapted for every one of those who have widely different degrees of difficulty in walking. The walker includes a pair of leg members each having a front wheel pivotable about a vertical shaft, a rear wheel and a pair of legs, and a support member detachably mounted on the leg members and having a pair of armrests and a support rod provided at one end thereof and extending in a width direction. The support member can be raised and lowered relative to the leg members and can be turned 180° so that its front and back are reversed relative to the leg members. It is thus possible to mount the support member so that the support rod is in front or back of the user according to the degree of difficulty in walking, posture and build of the user. It is also possible to adjust the height of the armrests by raising and lowering the support member relative to the leg members, as well as the distance between the armrests.

7 Claims, 10 Drawing Sheets

WALKER

BACKGROUND OF THE INVENTION

This invention relates to a walker used to help a handicapped person having difficulty in walking while supporting his or her body.

FIG. 14 shows a conventional walker, which comprises a frame 50 carrying at its bottom a pair of front wheels 51 and a pair of rear wheels 52. Each front wheel 51 is pivotable about a vertical shaft 53. A horseshoe-shaped armrest 54 is mounted on top of the frame 50 with its opening facing rearward.

A person with a walking problem can walk with this walker in any desired direction while supporting his or her arms on the armrest 54.

This walker, having an armrest that is closed at front and open at the rear, can stably support the body of a person with a rather serious walking problem at the front closed end of the armrest, because the upper torso of such a person is typically hunched forward. But this walker will be inconvenient for a person who has less difficulty in walking, because such a person can walk substantially in erect position and thus needs to be supported on his or her back. But the armrest of this walker cannot support the back of a user because its rear is open.

Another problem of this walker is that it is impossible to change the height or width of the armrest.

A user usually moves in a desired direction by leaning his or her body on the armrest. In order to stop, he or she has to stand rather firmly on his or her own foot or feet. For a person who cannot do this, it is a major problem to stop at a desired point.

An object of this invention is to provide a walker which is adapted for every one of those who have widely different degrees of difficulty in walking.

SUMMARY OF THE INVENTION

According to this invention, there is provided a walker comprising a pair of leg members each having a front wheel pivotable about a vertical shaft, a rear wheel and a pair of legs, and a support member detachably mounted on the leg members and having a pair of armrests and a support rod provided at one end thereof and extending in a width direction, wherein the support member can be raised and lowered relative to the leg members and can be turned 180° so that its front and back are reversed relative to the leg members and the distance between the armrests is adjustable.

According to this invention, according to the degree of difficulty in walking, posture and build of the user, it is possible to mount the support member on the leg members with its support rod located either at front or back of the walker, i.e. in front or back of the user, and to adjust the height of the armrests by raising and lowering the support member relative to the leg members, as well as the distance between the armrests.

By providing each rear wheel with the rotation resistance generator, it is possible to adjust the braking force applied to the rear wheel. For example, it is possible to increase the braking force when the walker is used by a person with a serious walking problem so that the walker will not move even if the user lean on the walker.

By providing each rear wheel with the reverse rotation preventive means, it is possible to prevent the walker from moving backward. Thus, the user can safely lean his or her back on the walker.

By providing each front wheel with the stopper, it is possible to keep the moving direction of the walker constant.

Other features and objects of the present invention will become apparent from the following description made with reference to the accompanying drawings, in which:

DETAILED DESCRIPTION OF THE PREFERRED EMBODIMENT

Figure 1:
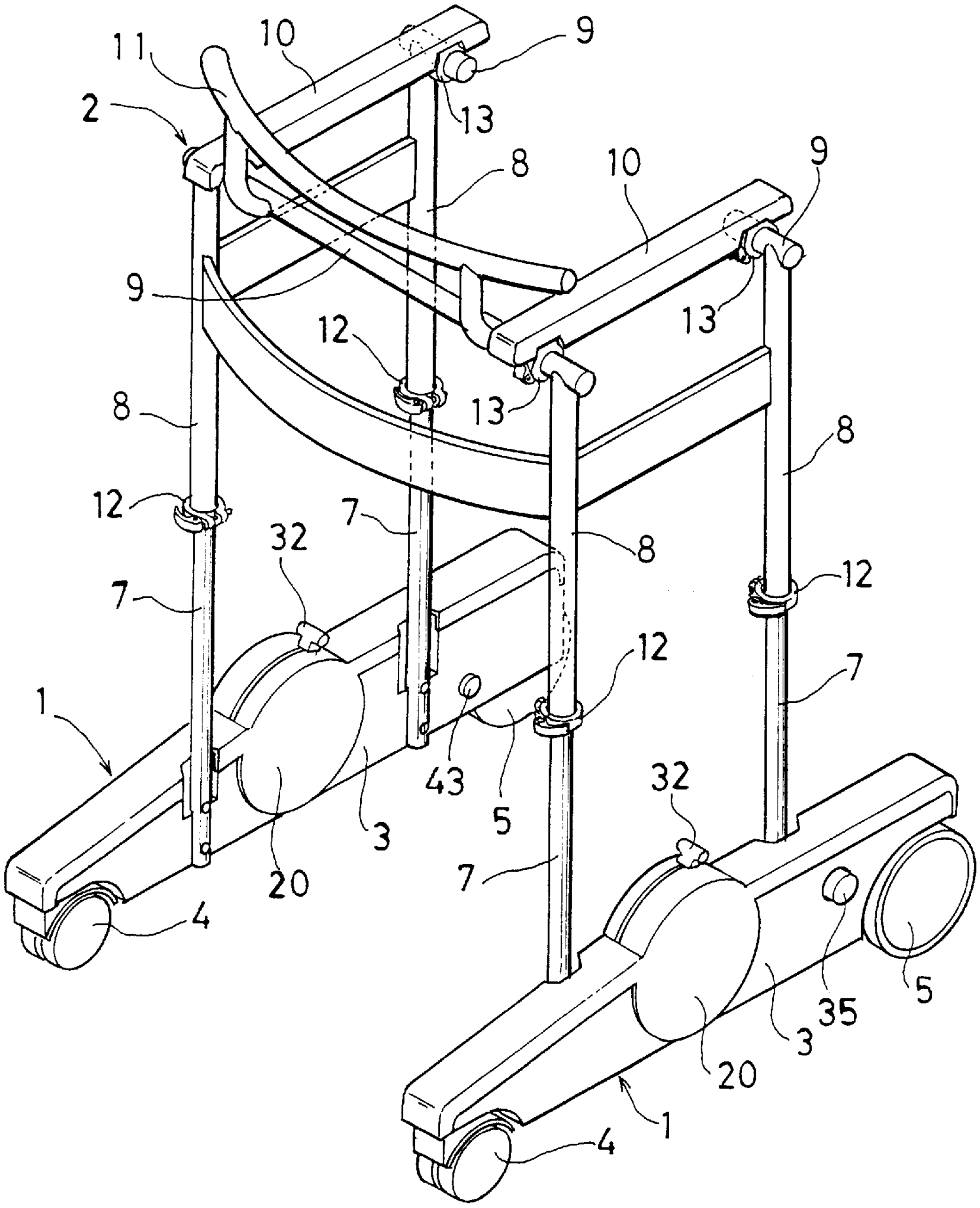
FIG. 1 is a perspective view of an embodiment of the walker according to this invention.
Figure 2:
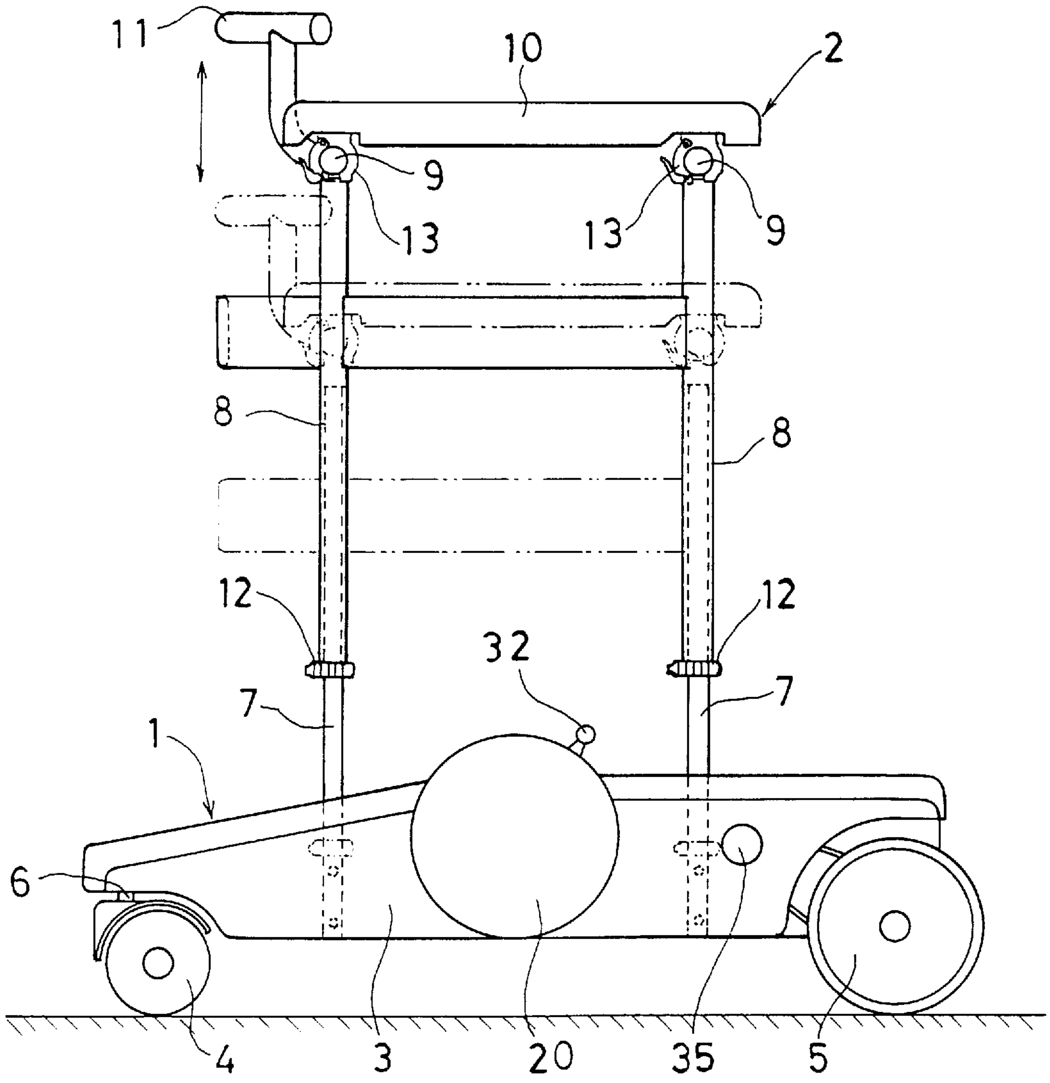
FIG. 2 is a side view thereof.

An embodiment of this invention is described with reference to the accompanying drawings. First referring to FIGS. 1 and 2, the walker of this embodiment comprises a pair of right and left leg members 1, and a support member 2 mounted on top of the leg members 1.

Each leg member 1 comprises a wheel carriage 3 carrying a front wheel 4 pivotable about a vertical shaft 6, and a rear wheel 5, and two legs 7 vertically extending from the inner side of the wheel carriage 3. The support member 2 comprises a pair of right and left armrests 10, and four vertical shafts 8 connected to the front and rear ends of the armrests 10 by mounting rods 9 and coupled to the respective legs 7, and plate members provided between the shafts 8 at one end of the support member 2 and between the two shafts 8 on either side of the support member. A support rod 11 extends widthwise over the armrests 10 at said one end of the support member 2.

The shafts 8 are tubular members having bottom openings into which are slidably inserted the respective legs 7. The legs 7 and shafts 8 are fixed together by clamps 12. By loosening the clamps 12, the support member 2 can be raised or lowered relative to the leg members 1 or pulled upwardly out of the leg members 1.

The armrests 10 are slidable relative to the mounting rods 9 and can be fixed to the mounting rods 9 by clamps 13. By loosening the clamps 13, the armrests 10 can be moved in the width direction of the support member 2.

Figure 3:
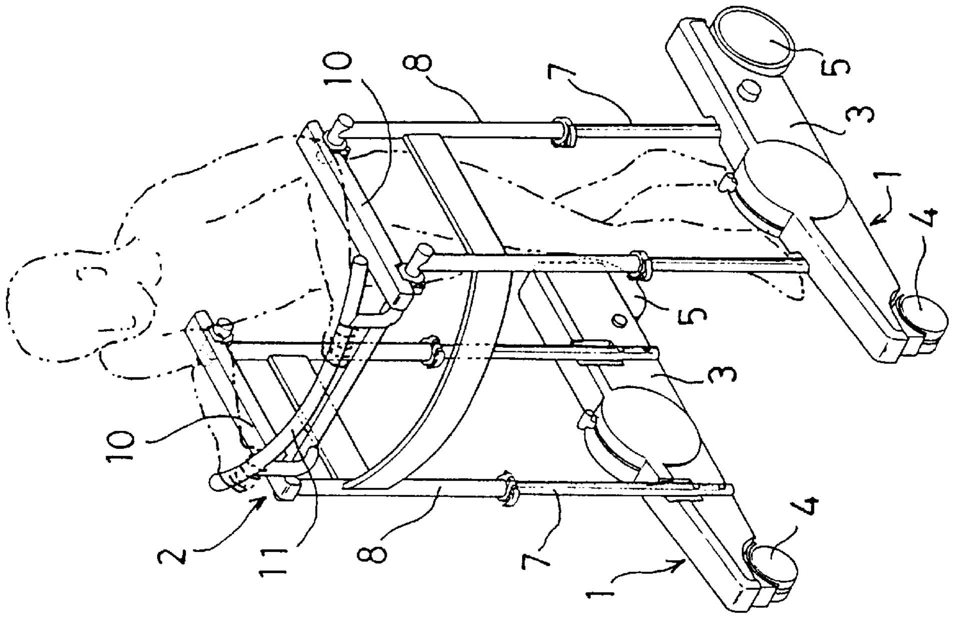
FIGS. 3–5 are perspectives views thereof showing different states of use.

If this walker is to be used by a person with a rather serious walking problem, the support member 2 is mounted so that the support rod 11 is at the front end of the walker. Thus, this person can walk while gripping the support rod 11 with his or her forearms resting on the armrests with the arms folded, as shown in FIG. 3.

Figure 4:
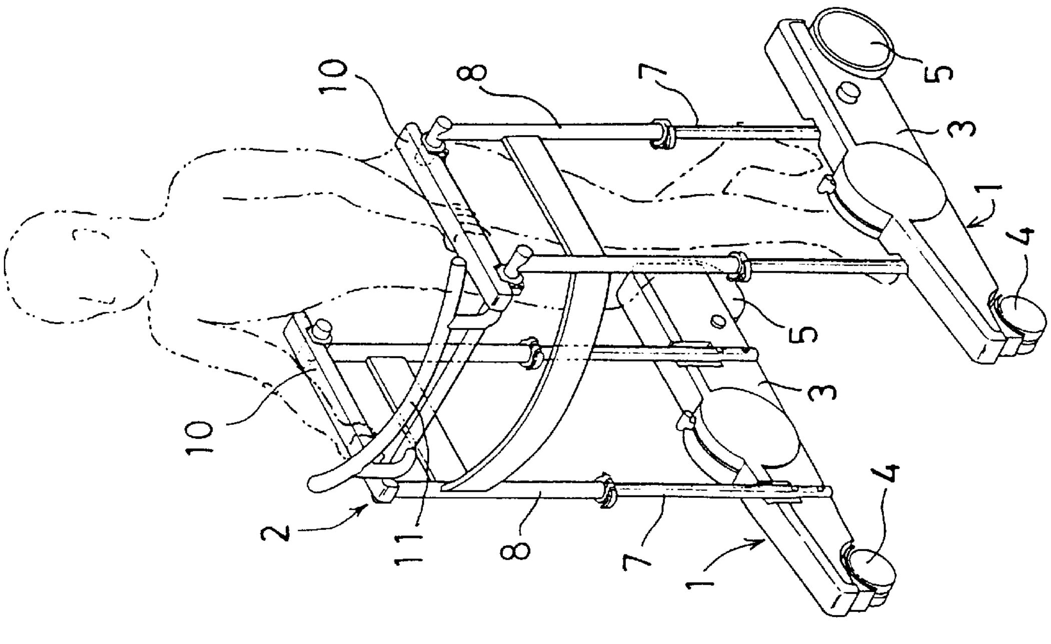
Figure 5:
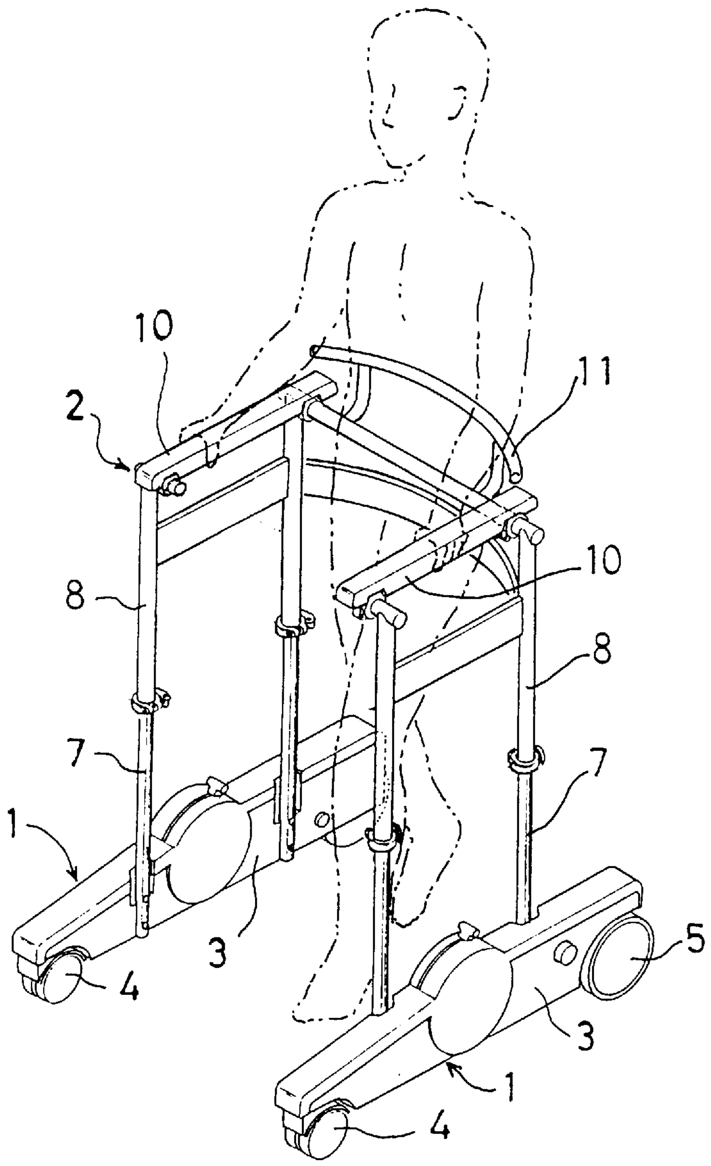

If the walker is to be used by a person with a medium degree of walking problem, who can walk with his upper torso more or less erect and with his or her arms straightened and put on the armrests 10 as shown in FIG. 4, he or she can always support his or her body on the support rod 11. This can give the user a sense of security.

If this walker is to be used by a person with a lighter degree of walking problem, who can walk substantially in an erect posture, the support member 2 is pulled up out of the leg members 1, turned 180° horizontally, and coupled to the leg members 1 again so that the support rod 11 is positioned at the back of the walker. In this arrangement, the support rod 11 is used to support the back of the user.

According to the build and posture of the user, it is possible to adjust the height of the armrests 10 by raising and lowering the support member 2 relative to the leg members 1 and the distance between the armrests 10 by moving them in the width direction of the support member 2.

Figure 6A:
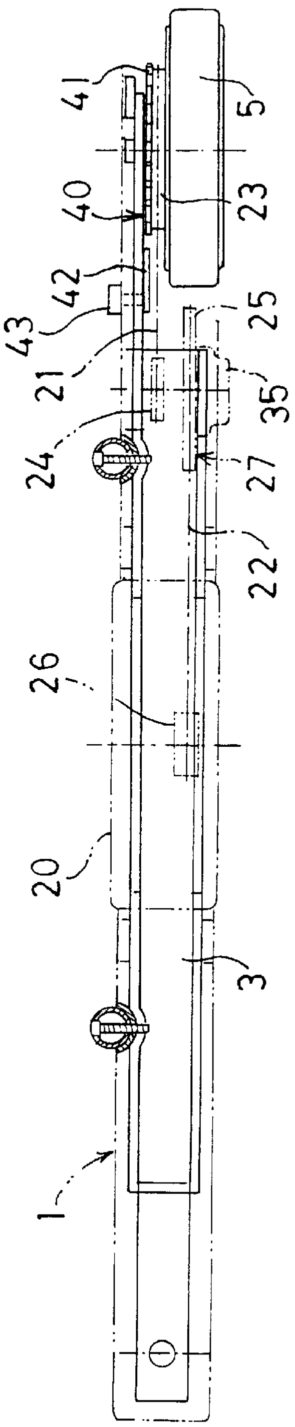
FIG. 6A is a schematic plan view of a wheel carriage thereof.
Figure 6B:
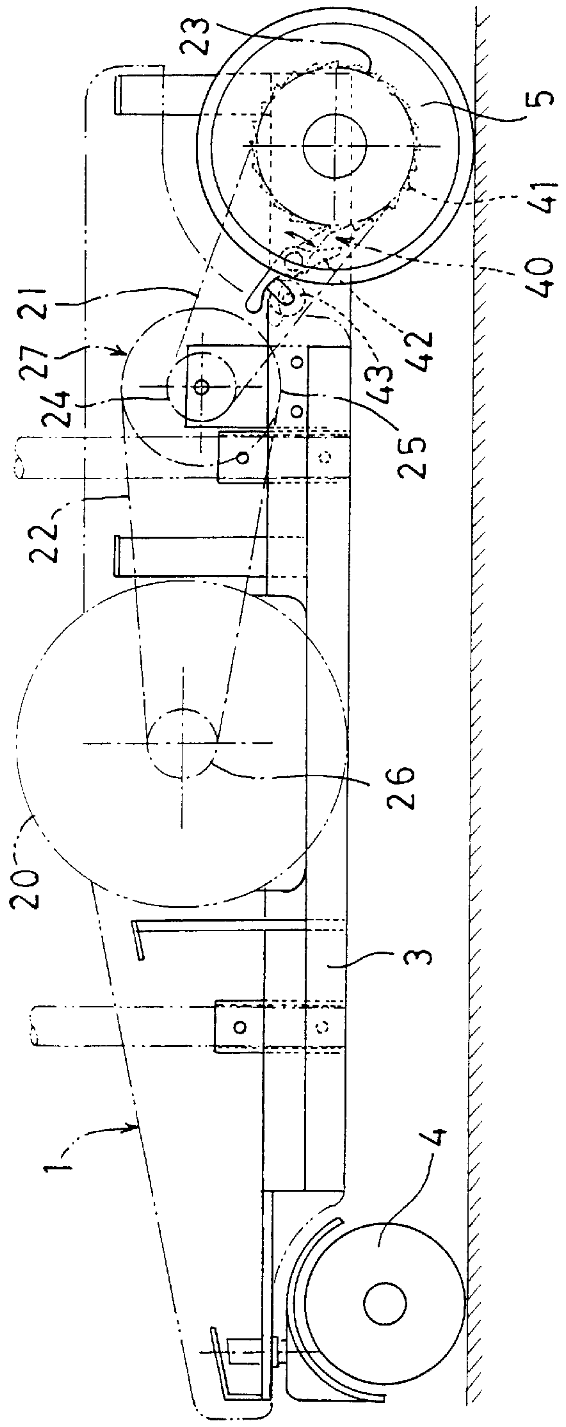
FIG. 6B is a schematic side view thereof.

As shown in FIG. 6, a rotation resistance generator 20 is provided in the center of each wheel carriage 3. To each rotation resistance generator 20, the rotation of the rear wheel 5 is transmitted through endless belts 21, 22. The belt 21 extends around pulleys 23 and 24, while the belt 22 extends around pulleys 25 and 26. Fixed to a rotary shaft of the rear wheel 5, the pulley 23 rotates with the rear wheel 5. The pulleys 24 and 25, arranged coaxially with each other, serves as a clutch 27. The pulley 26 is mounted in the rotation resistance generator 20. The pulleys 23 to 26 and the belts 21, 22 are all toothed and in mesh with each other.

Figure 7:
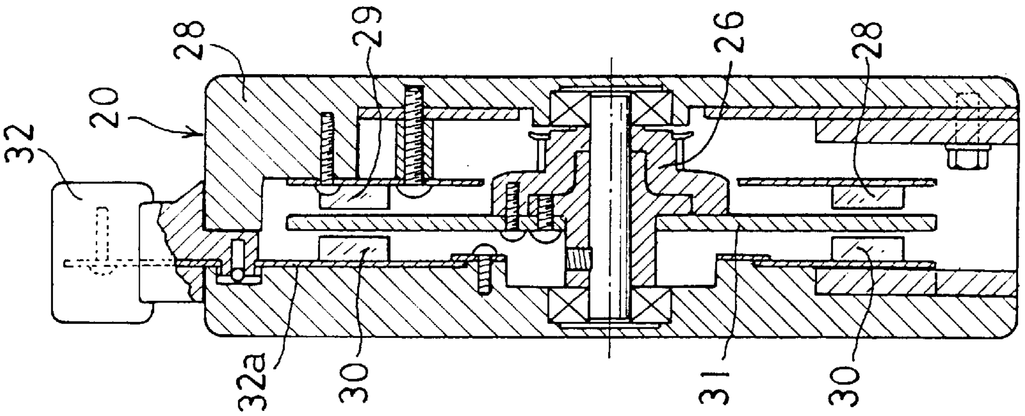
FIG. 7 is a vertical sectional side view of a rotation resistance generator.
Figure 8:
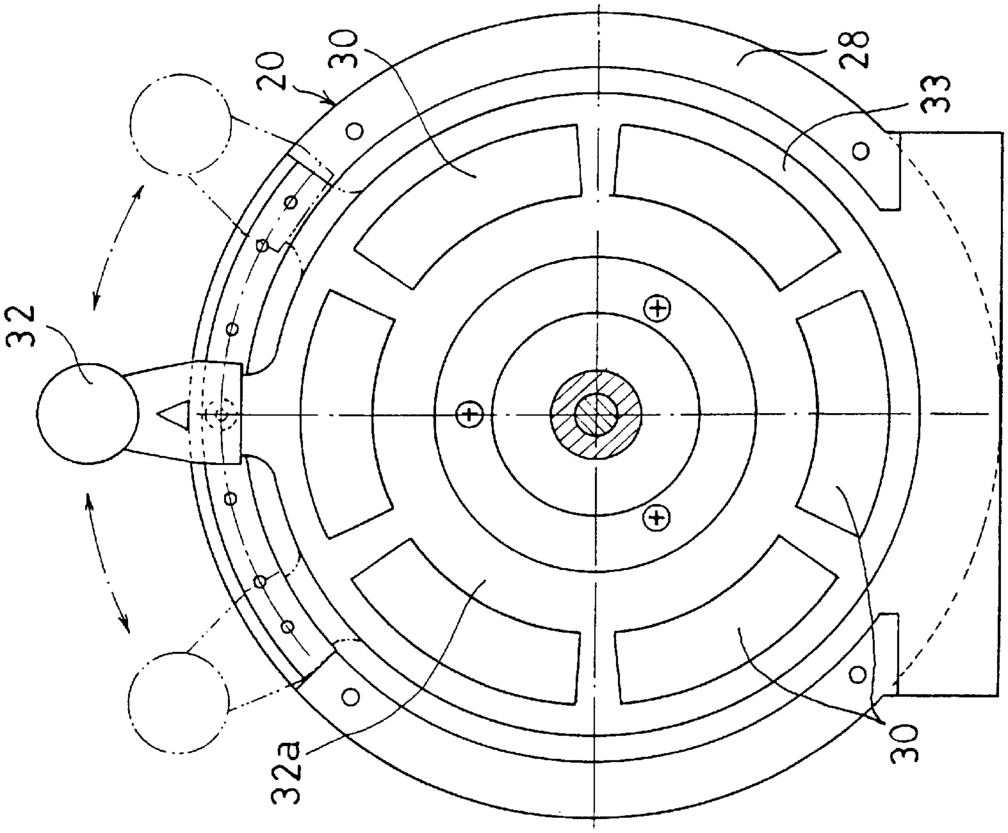
FIG. 8 is a vertical sectional front view of the same at movable magnet side.
Figure 9:
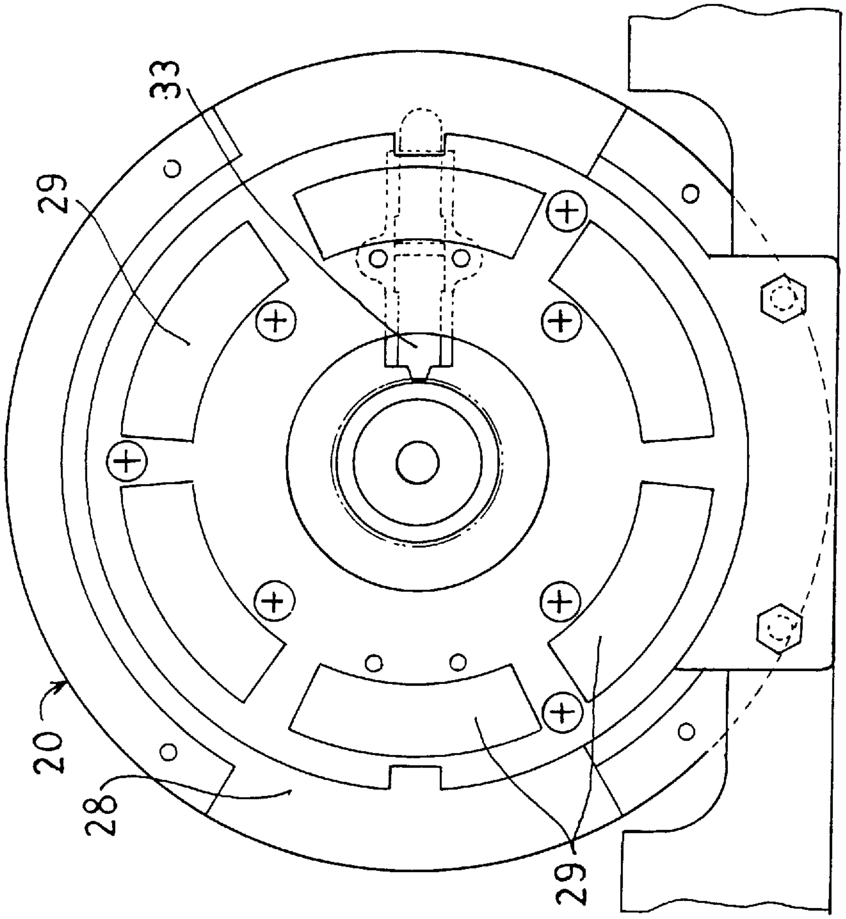
FIG. 9 is a vertical sectional front view of the same at fixed magnet side.

As shown in FIGS. 7–9, each rotation resistance generator 20 has magnets 29, 30 provided in a case 28 opposite to each other, and a metallic rotary plate 31 provided between the magnets 29, 30 and adapted to rotate together with the pulley 26. As the rotary plate 31 rotates, rotation resistance resulting from eddy current produced on its surface is applied to the pulley 26, thus braking the rear wheel 5.

The magnet 29 is fixed to the case 28, while the other magnet 30 is mounted on a support plate 32*a* which can be rotated relative to the case 28, coupled with a lever 32. Thus, by operating the lever 32, the relative position between the magnets 29 and 30 and the rotation resistance applied to the pulley 26 change, so that it is possible to adjust the braking force applied to the rear wheel 5. Further, a brake 33 is mounted in the case 28. By operating the lever 32, it is possible to move the brake 33 into mesh with the pulley 26, thereby completely stopping the rotation of the pulley 26 and locking the rear wheel 5.

Figure 10:
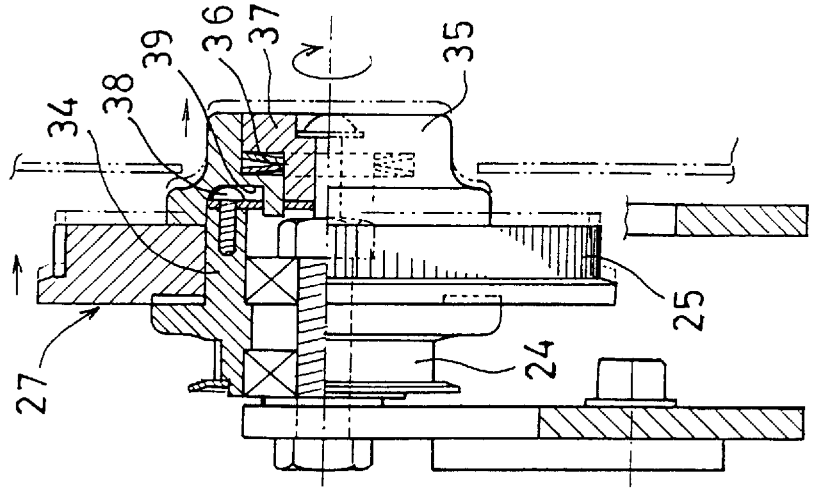
FIG. 10 is a vertical sectional side view of a clutch of the same.
Figure 11:
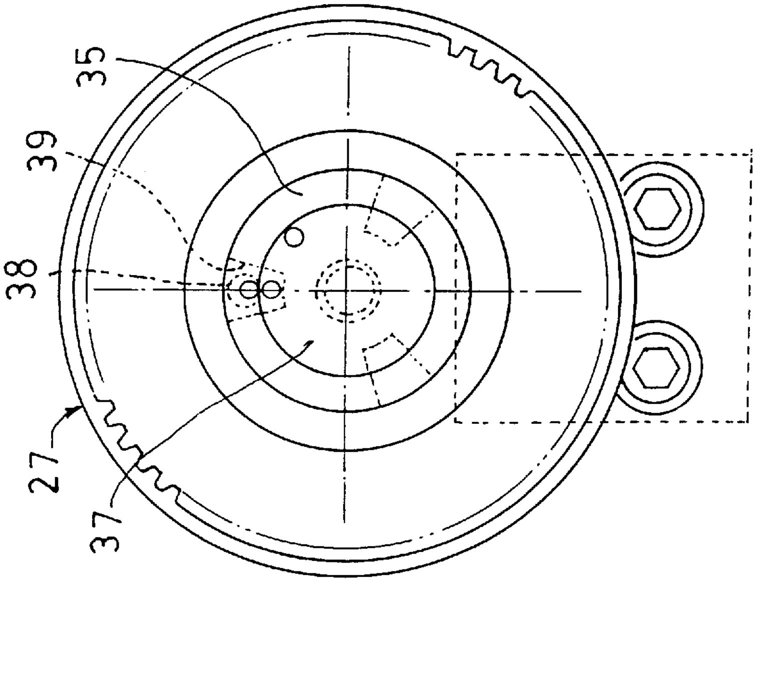
FIG. 11 is a schematic front view thereof.

Now referring to FIGS. 10 and 11, the pulley 24 of the clutch 27 has a boss 34 slidably fitted in the pulley 25. The boss 34 carries on its end face a knob 35 that is rotatable by a predetermined angle, and a knob core 37 biasing the knob 35 against the pulley 25 through a disc spring 36. As the knob 35 rotates, the head of a mounting screw 38 of the knob core 37 engages and disengages from a recess 39 formed in the back of the knob 35. Thus, the knob 35 and the pulley 25 are moved in the axial direction of the boss 34, so that the pulleys 24 and 25 can be connected and disconnected.

If the walker is to be used by a person with a serious walking problem, the levers 32 are moved to a position where a large braking force is applied to the rear wheels 5 so that the walker would not move simply by leaning the user's body against the walker.

If there is no need to brake the rear wheels 5, the pulleys 24 and 25 are disengaged from each other by turning the knob 35.

Each rear wheel 5 has, as seen in FIG. 6, a reverse rotation preventive mechanism 40. This reverse rotation preventive mechanism 40 comprises a ratchet wheel 41 nonrotatably mounted on the rear wheel 5, and a claw 42 urged toward the outer periphery of the ratchet wheel 41. This mechanism can be disengaged by moving the claw 42 away from the ratchet wheel 41 by turning a knob 43.

While the reverse rotation preventive mechanism 40 is in engagement, the walker will not move backward, so that the user can safely lean his or her back on the walker.

Figure 12A:
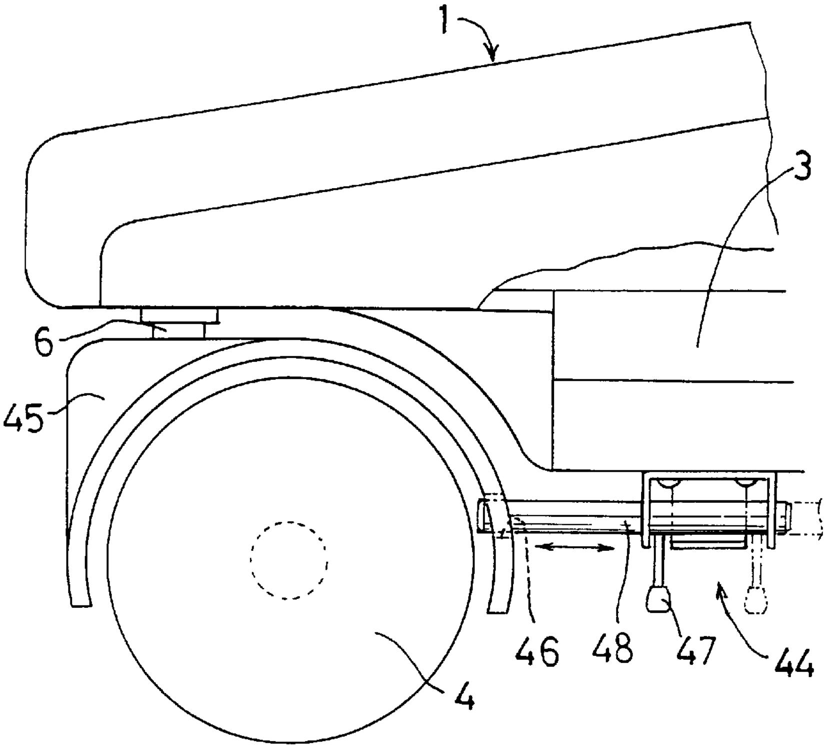
FIG. 12A is a side view of a stopper for a front wheel.
Figure 12B:
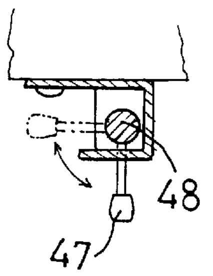
FIG. 12B is its partial vertical front view.
Figure 13:
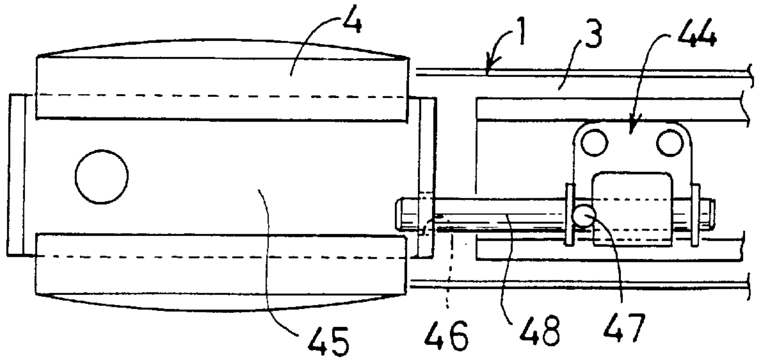
FIG. 13 is its bottom view.
Figure 14:
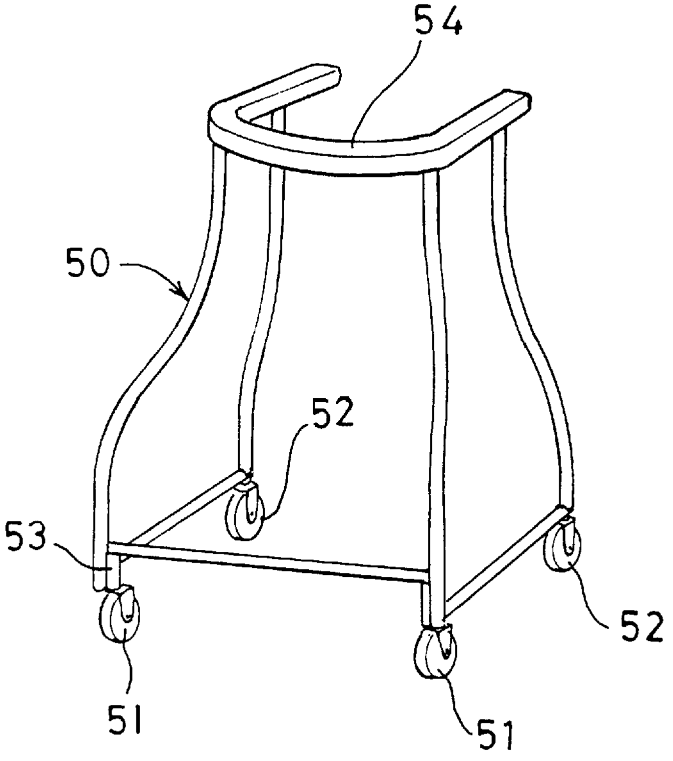
FIG.14 PRIOR ART
FIG. 14 is a perspective view of a conventional walker.

As shown in FIGS. 12 and 13, each front wheel 4 has a stopper 44 which includes a pin 48 which is moved into and out of a hole 46 formed in a front wheel cover 45 by operating a lever 47. When the pin 48 is inserted in the hole 46, the front wheel 4 cannot rotate. As the pin 48 rotates, the lever 47 pivots about the pin 48. When the lever 47 is in its horizontal position, the pin 48 can move into and out of the hole 46. When the lever is turned down, the pin cannot move.

When the front wheels 4 are locked by the respective stoppers 44, it is possible to keep constant the moving direction of the walker especially when the user's back is leaned against the walker.

What is claimed is:

1. A walker comprising a pair of leg members each having a front wheel pivotable about a vertical shaft, a rear wheel and a pair of legs, and a support member detachably mounted on said leg members and having a pair of armrests and a support rod provided at one end thereof and extending in a width direction, wherein said support member can be raised and lowered relative to said leg members and can be turned 180° so that its front and back are reversed relative to said leg members and the distance between said armrests is adjustable.

2. A walker as claimed in claim 1 wherein each of said rear wheels is provided with a rotation resistance generating means for adjusting braking force.

3. A walker as claimed in claim 1 or 2 wherein each of said rear wheels is provided with a reverse rotation preventive means.

4. A walker as claimed in claim 3 wherein each front wheel is provided with a stopper means for preventing said front wheels from pivoting.

5. A walker as claimed in claim 2 wherein each of said rear wheels is provided with a reverse rotation preventive means.

6. A walker as claimed in claim 2 wherein each front wheel is provided with a stopper means for preventing said front wheels from pivoting.

7. A walker as claimed in claim 1 wherein each front wheel is provided with a stopper means for preventing said front wheels from pivoting.

* * * * *